US 7,987,696 B2

(12) United States Patent
Kuronita et al.

(10) Patent No.: US 7,987,696 B2
(45) Date of Patent: Aug. 2, 2011

(54) FUEL DISTILLATION PROPERTY DETERMINING APPARATUS AND METHOD

(75) Inventors: Tokuji Kuronita, Kariya (JP); Satoru Sasaki, Kariya (JP)

(73) Assignee: Denso Corporation, Kariya (JP)

( * ) Notice: Subject to any disclaimer, the term of this patent is extended or adjusted under 35 U.S.C. 154(b) by 462 days.

(21) Appl. No.: 12/332,597

(22) Filed: Dec. 11, 2008

(65) Prior Publication Data

US 2009/0145199 A1 Jun. 11, 2009

(30) Foreign Application Priority Data

Dec. 11, 2007 (JP) .................................. 2007-319699

(51) Int. Cl.
*G01N 33/22* (2006.01)
(52) U.S. Cl. ...................................................... 73/35.02
(58) Field of Classification Search .................. 73/35.02, 73/114.38
See application file for complete search history.

(56) References Cited

U.S. PATENT DOCUMENTS

| 6,907,861 | B2 | 6/2005 | Asano et al. | |
|---|---|---|---|---|
| 7,246,596 | B2* | 7/2007 | Yamaguchi et al. | 123/299 |
| 7,401,591 | B2* | 7/2008 | Yamaguchi et al. | 123/299 |
| 7,421,884 | B2* | 9/2008 | Aoyama | 73/35.02 |
| 7,621,174 | B2* | 11/2009 | Takaku | 73/114.53 |
| 7,630,824 | B2* | 12/2009 | Hirata | 701/105 |
| 7,926,331 | B2* | 4/2011 | Tsutsumi et al. | 73/114.38 |
| 2007/0151542 | A1 | 7/2007 | Yamaguchi et al. | |

FOREIGN PATENT DOCUMENTS

| JP | 2005-023856 | 1/2005 |
|---|---|---|
| JP | 2005-36788 | 2/2005 |
| JP | 2006-226188 | 8/2006 |
| JP | 2007-154802 | 6/2007 |

OTHER PUBLICATIONS

Japanese Office Action dated May 11, 2010, issued in corresponding Japanese Application No. 2007-319699, with English translation.

* cited by examiner

*Primary Examiner* — Freddie Kirkland, III
(74) *Attorney, Agent, or Firm* — Nixon & Vanderhye PC

(57) ABSTRACT

A fuel distillation property determining apparatus for use in a multi-injection system for diesel engines. The apparatus acquires a physical quantity indicating a state of burning of fuel in the diesel engine, determines a physical quantity variation sensitivity defined by a ratio of a quantity variation that is a difference between a first value of the physical quantity, as acquired upon execution of a first one of a sequence of sub-injections, and a second value of the physical quantity, as acquired upon execution of a following one of the sub-injections, to a difference between a first quantity of fuel sprayed in the first sub-injection and a second quantity of fuel sprayed in the following sub-injection, and determine a cetane value of the fuel based on a predefined relation between the physical quantity variation sensitivity and the cetane value. This ensures the accuracy in determining the cetane value at low costs.

8 Claims, 9 Drawing Sheets

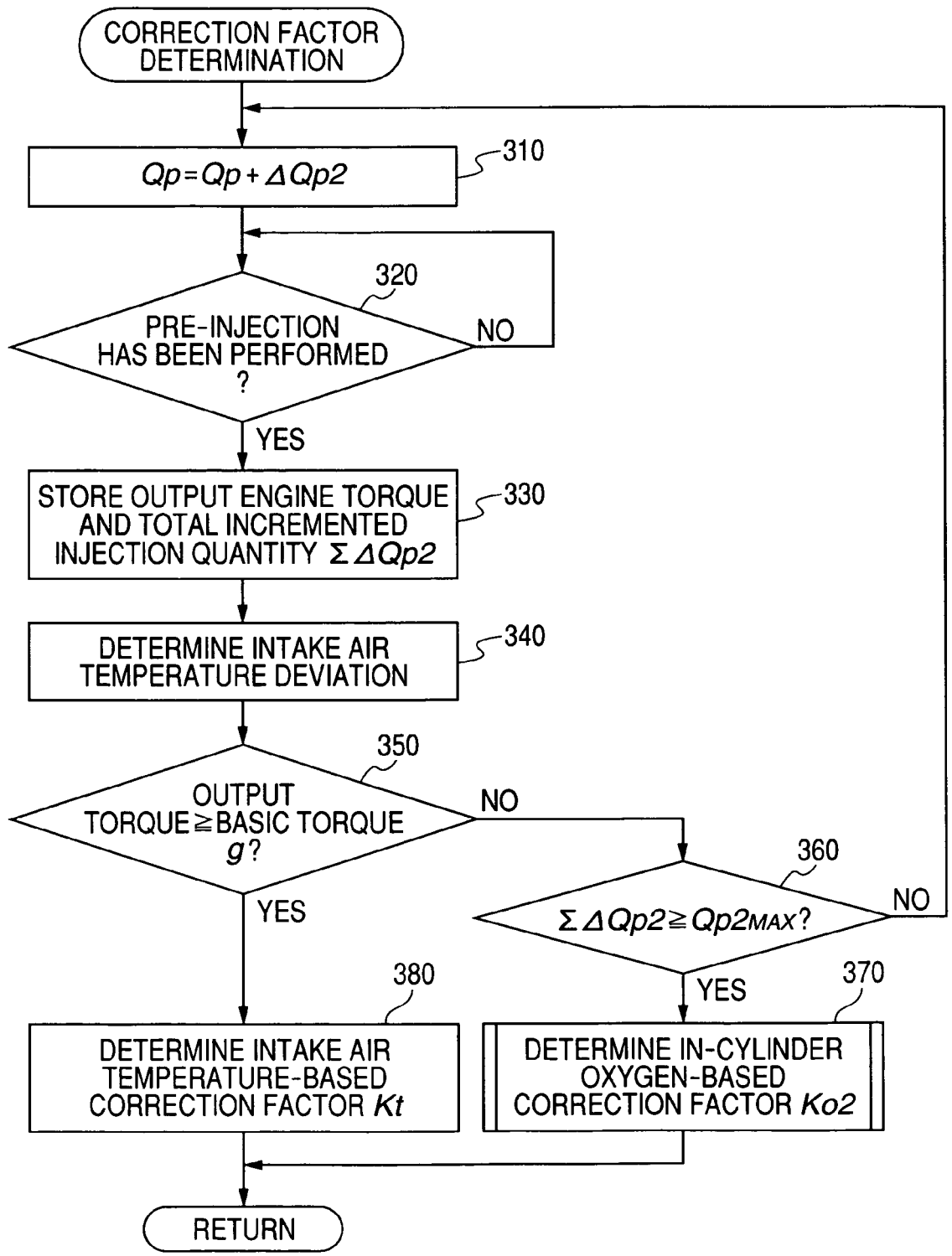

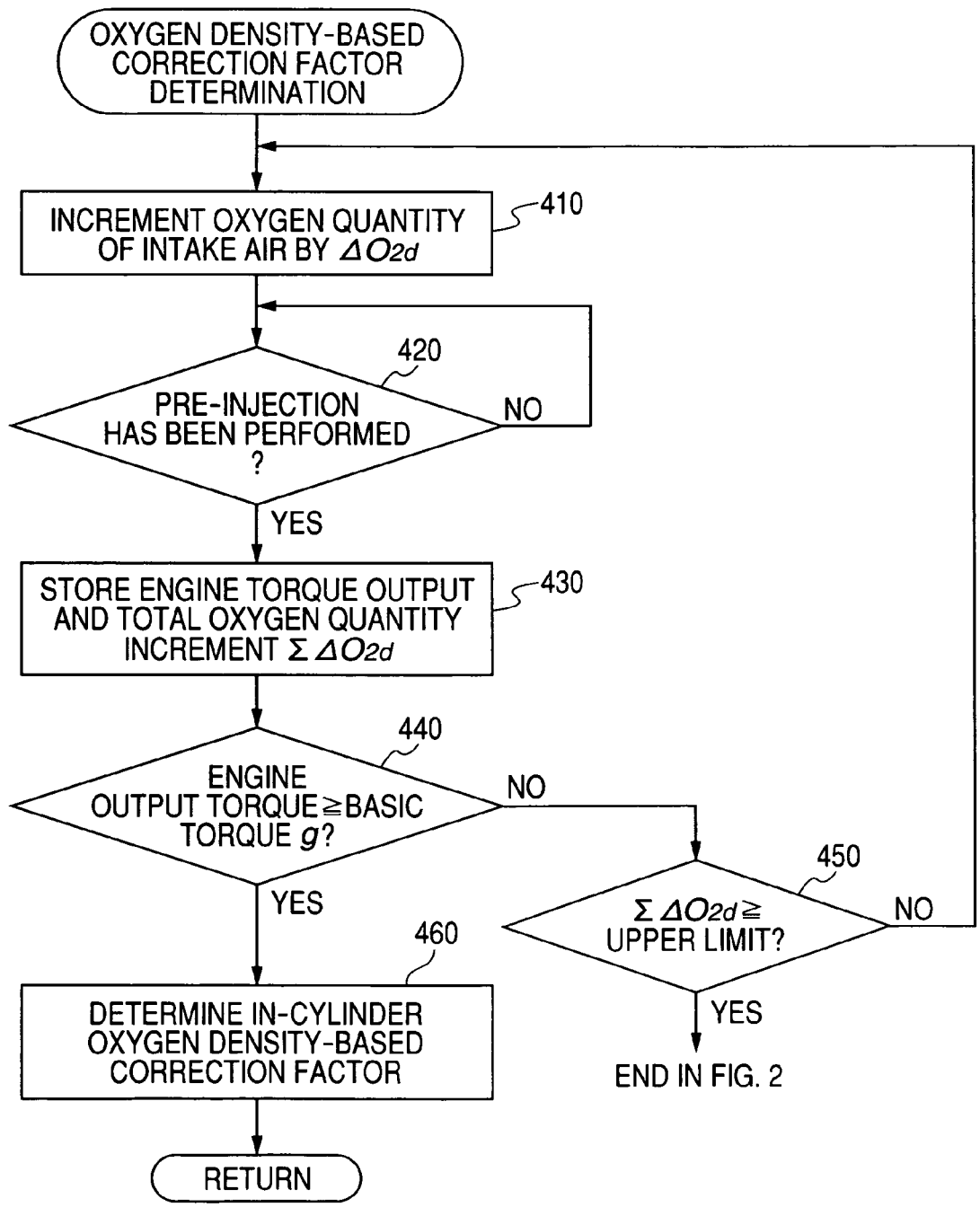

FUEL DISTILLATION PROPERTY DETERMINING APPARATUS AND METHOD

CROSS REFERENCE TO RELATED DOCUMENT

The present application claims the benefit of Japanese Patent Application No. 2007-319699 filed on Dec. 11, 2007, the disclosure of which is incorporated herein by reference.

BACKGROUND OF THE INVENTION

1. Technical Field of the Invention

The present invention relates generally to a fuel distillation property determining apparatus designed to determine the distillation property of fuel used in diesel engines and a method of determining such a fuel distillation property.

2. Background Art

Modern fuel injection systems for automotive diesel engines are designed to perform a multi-injection control mode in which a sub-injection(s) of fuel is executed preceding or following a main injection for reducing combustion noise and NOx emissions.

It is essential for ensuring beneficial effects of the multi-injection control mode to measure the distillation property (especially, the cetane value also called cetane number) of used fuel such as light oil to correct the quantity of fuel to be injected into the engine or the injection timing thereof.

Japanese Patent First Publication No. 2005-23856 teaches a fuel distillation property measuring method of sampling the speed of the diesel engine for a given number of cycles to determine a difference between a maximum and a minimum speed (which will also be referred to as an engine speed variation below) and determining the distillation property of the fuel based on the engine speed variation. Specifically, when the engine speed variation is greater than a given reference value, the fuel is determined to be low volatile. Alternatively, when the engine speed variation is lower than the given reference value, the fuel is determined to be high volatile.

Japanese Patent First Publication No. 2006-226188 teaches use of an in-cylinder pressure sensor to measure the pressure in a cylinder of the diesel engine to calculate the time when the fuel has been ignited and the amount of burned fuel (i.e., the quantity of heat that is a parameter representing engine output torque) in the sub-injection mode for determining the cetane value of the fuel based thereon.

Usually, the diesel engines are subjected to a great change in speed thereof depending upon the temperature of ambient air or the property of air sucked into the cylinder of the engine even when a constant quantity of fuel is sprayed cyclically into the engine without changing the distillation property of the fuel.

The method, as taught in the former publication, therefore, encounters the drawback in that it is difficult to determine whether the change in speed of the diesel engine is caused by a change in distillation property of the fuel or another factor accurately.

The in-cylinder pressure sensor is usually used for measuring the pressure in the cylinder of the engine in the main injection mode and thus unsuitable for measuring a change in pressure in the cylinder when a small quantity of fuel (approximately 1/30 of that in the main injection mode) is sprayed, for example, in the sub-injection mode to determine whether the pressure change has resulted from the burning of the fuel or some electrical noise added to the output of the in-cylinder pressure sensor. It may, therefore, be impossible to the ignition timing or the amount of burned fuel in the sub-injection mode. The system, as taught in the latter publication, has also the problem that it is difficult to determine the fuel distillation property accurately.

SUMMARY OF THE INVENTION

It is therefore a principal object of the invention to avoid the disadvantages of the prior art.

It is another object of the invention to provide a fuel distillation property determining apparatus and method for determining the cetane value of fuel accurately.

According to one aspect of the invention, there is provided a fuel distillation property determining apparatus designed to determine a cetane value of fuel to be injected into a diesel engine by a fuel injection system. The fuel injection system works to perform, in a cycle, a sub-injection which injects an injection quantity that is a quantity of the fuel smaller than that in a main injection into the diesel engine at a time when the fuel is to be burned in the diesel engine preceding or following the main injection. The fuel distillation property determining apparatus comprises: (a) sub-injection control means for controlling the fuel injection system to perform a sequence of the sub-injections, a first one of the sub-injections being to spray a first quantity of the fuel as the injection quantity, a following one of the sub-injections being to spray a second quantity of the fuel as the injection quantity which is different from the first quantity; (b) physical quantity acquiring means for acquiring a given physical quantity indicating a state of burning of the fuel in the diesel engine; (c) physical quantity variation sensitivity determining means for determining a physical quantity variation sensitivity which is defined by a ratio of a quantity variation that is a difference between a first value of the physical quantity, as acquired upon execution of the first one of the sub-injections, and a second value of the physical quantity, as acquired upon execution of the following one of the sub-injections, to a difference between the first quantity and the second quantity; and (d) fuel distillation property determining means for determining a cetane value of the fuel based on a predefined relation between the physical quantity variation sensitivity and the cetane value.

Specifically, the fuel distillation property determining apparatus works to instruct the fuel injection system to perform at least two injections which are different in quantity of fuel to be sprayed into the diesel engine and calculate a ratio (i.e., the physical quantity variation sensitivity) of a change in the physical quantity between events of the two injections to a change in sprayed quantity of the fuel between the events of the two injections. The fuel distillation property determining apparatus determines the cetane value (also called a cetane number) of the fuel based on the ratio (i.e., the physical quantity variation sensitivity).

The physical quantity variation sensitivity, therefore, hardly changes with a change in operating condition or operating environment of the diesel engine, thus resulting in increased accuracy in determining the cetane value of the fuel. This enables the cetane value to be used to control the timing of the sub-injection, the quantity of the fuel to be injected, and the quantity of exhaust gas emitted from the diesel engine to be recirculated to the cylinder of the diesel engine for reducing harmful emissions such as NOx, smoke, HC, and Co from the diesel engine.

The fuel distillation property determining apparatus eliminates the need for an additional sensor, thereby permitting the fuel distillation property determining apparatus to be manufactured at low costs while ensuring the accuracy of determination of the cetane value.

The physical quantity, as referred to herein, is a parameter which increases as the amount of burned fuel in the diesel engine increases. The physical quantity variation sensitivity is a parameter so that the greater the parameter, the greater the cetane value.

In the preferred mode of the invention, the fuel distillation property determining apparatus further includes engine environment indicative parameter acquiring means for acquiring an engine environment indicative parameter representing an engine operating environment when the diesel engine is running, engine operation indicative parameter acquiring means for acquiring an engine operation indicative parameter representing an operating condition of the diesel engine, intake air indicative parameter acquiring means for acquiring an intake air indicative parameter representing a status of intake air to be sucked into a cylinder of the diesel engine, and cetane value determination permission means for permitting the fuel distillation property determining means to determine the cetane value when at least one of the engine environment indicative parameter, the engine operation indicative parameter, and the intake air indicative parameter is in a given permissible range.

Specifically, when the diesel engine is running so as to meet a given operating condition, the fuel distillation determining apparatus allows the cetane value to be determined, thus increasing the accuracy in determining the cetane value.

It is advisable that when the engine environment indicative parameter, the engine operation indicative parameter, and the intake air indicative parameter are all within given permissible ranges, respectively, the cetane value be allowed to be determined in order to improve the accuracy in determining the cetane value further.

When at least one of the engine environment indicative parameter, the engine operation indicative parameter, and the intake air indicative parameter lies within the given permissible range, the sub-injection control means preferably controls the fuel injection system to spray the first quantity of the fuel and the second quantity of the fuel in sequence and permits the fuel distillation property determining means to determine the cetane value.

The engine environment indicative parameter, as referred to herein is the temperature of the intake air charged into the cylinder of the diesel engine or the atmospheric pressure. The engine operation indicative parameter is the speed of the diesel engine or the quantity of fuel sprayed in the sub-injection or the main injection. The intake air indicative parameter includes at least the quantity of the intake air charged into the cylinder of the diesel engine. In the case where the diesel engine is equipped with a recirculating mechanism working to recirculate exhaust gas emitted from the diesel engine to the cylinder of the diesel engine, the intake air indicative parameter preferably includes a ratio of the amount of the recirculated exhaust gas to the whole of the intake air (i.e., the EGR rate).

The fuel distillation property determining apparatus may further comprise comprising factor determining means for determining whether the first value, as acquired upon execution of the first one of the sub-injections, lies out of a given range or not which is defined based on a value of the physical quantity which is to appear when the sub-injection is executed. When it is determined that the first value is out of the given range, and when the cetane value determination permission means permits the fuel distillation property determining means to determine the cetane value, the factor determining means makes a determination of which of a temperature of intake air and an in-cylinder oxygen density is a factor causing the first value to lie out of the given range. The temperature of the intake air is the temperature of air to be sucked into a cylinder of the diesel engine. The in-cylinder oxygen density is the density of oxygen contained in the air sucked in the cylinder of the diesel engine. The fuel distillation property determining apparatus may also comprise correcting means for correcting the cetane value, as derived by the fuel distillation property determining means, based on the determination of the factor determining means.

Specifically, the fuel distillation property determining apparatus works to correct the cetane value based on the factor causing the first value of the physical quantity, as acquired upon execution of the first one of the sub-injections, is out of the given range, thus bringing the cetane value toward a correct value.

The in-cylinder oxygen density is a parameter which indicates a ratio of the quantity (the mass or volume) of oxygen contained in the intake air charged into the cylinder of the diesel engine to the quantity (the mass or volume) of the intake air and which may be derived by dividing the mass of oxygen in the intake air by the volume of a clearance between an inner wall of the cylinder and the head of a piston in the cylinder when the piston is at the top dead center in a compression stroke thereof.

The factor determining means may include injection quantity changing means and intake air flow controlling means. The injection quantity changing means changes the injection quantity by a given amount each time the sub-injection is made until a total of the amounts reaches an upper limit. After the injection quantity changing means changes the injection quantity until the total of the amounts reaches the upper limit, the intake air flow controlling means controls a regulator mechanism which works to mix atmospheric air with exhaust gas emitted from the diesel engine to produce the intake air and regulate a quantity of the atmospheric air and a quantity of the exhaust gas in the intake air to increase the in-cylinder oxygen density. When the physical quantity, as acquired by the physical quantity acquiring means, falls in the given range before the injection quantity in the sub-injection, as changed by the injection quantity changing means, reaches the upper limit, the factor determining means determines the temperature of intake air as being the factor causing the first value to lie out of the given range. When the physical quantity, as acquired by the physical quantity acquiring means, falls in the given range upon execution of the sub-injection after the in-cylinder oxygen density is increased by the intake air flow controlling means, the factor determining means determines the in-cylinder oxygen density as being the factor causing the first value to lie out of the given range.

The injection quantity changing means may reset the changed injection quantity as the first quantity. The sub-injection control means may instruct the fuel injection system to spray the reset first quantity of fuel into the diesel engine.

The inventors of this application have found, as illustrated in FIG. 8, that when the in-cylinder oxygen density is smaller than a given value (e.g., 2.0 g/cm$^3$), the fuel sprayed into the diesel engine will fail to be burned regardless of the quantity of the fuel which means that it is impossible to acquire the physical quantity and that when the in-cylinder oxygen density is greater than or equal to the given value (e.g., 2.0 g/cm$^3$), the amount of burned fuel (i.e., the burning rate) will increase with an increase in the in-cylinder oxygen density until the amount of burned fuel reaches a maximum amount which depends upon the kind of the fuel. The inventors also have found that the higher the cetane value of the fuel used in the diesel engine (see higher cetane value fuel, middle cetane value fuel, and lower cetane value fuel in FIG. 8, the greater the density of oxygen in the cylinder required to achieve the maximum amount of burned fuel. FIG. 8 demonstrates a relation between the in-cylinder oxygen density and the amount of burned fuel (or the burning rate) in the condition where a constant quantity of fuel is sprayed in the sub-injection for each kind of the fuel.

A method of determining the cetane value of the fuel using the above evidence found by the inventors may be achieved by changing, for example, incrementing the in-cylinder oxygen density each execution of the sub-injection during an interval from when the in-cylinder oxygen density shows the given value to when the in-cylinder oxygen density has a value establishing the maximum amount of burned fuel, determining the value of the in-cylinder oxygen density when the amount of burned fuel reaches a given value, and calculating the cetane value based on the determined value of the in-cylinder oxygen density. The cetane value may alternatively be determined by changing, for example, incrementing the in-cylinder oxygen density each execution of the sub-injection, finding the value of the in-cylinder oxygen density when the maximum amount of burned fuel is reached, for example, when the amount of burned fuel becomes unchanged, and calculating the cetane value based on the found value of the in-cylinder oxygen density.

In order to derive the cetane value more accurately, the correcting means may include factor determining means for determining the in-cylinder oxygen density. Specifically, when the factor determining means determines the in-cylinder oxygen density as being the factor causing the first value to lie out of the given range, the correcting means corrects the cetane value so as to decrease as the in-cylinder oxygen density, as determined by the oxygen density determining means, is higher than a given oxygen density.

The correcting means may also include temperature determining means for determining the temperature of the intake air. Specifically, when the factor determining means determines the temperature of the intake air as being the factor causing the first value to lie out of the given range, the correcting means corrects the cetane value so as to decrease as a value of the temperature of the intake air, as determined by the temperature determining means, becomes higher than a value of the temperature of the intake air when being in the given permissible range (i.e., the reference temperature as will be described later in detail).

The physical quantity, as acquired by the physical quantity acquiring means, may be one of a work of the diesel engine and a variation in speed of the diesel engine. This eliminates the need for an in-cylinder pressure sensor, as used in the above discussed Japanese Patent First Publication No. 2006-226188, thus permitting the cetane value of the fuel to be determined at low costs.

The work, as referred to therein, is a parameter indicating a work as produced when the diesel engine is being subjected to the sub-injection of fuel and may be defined by the output torque of the diesel engine, the amount of burned fuel, or the speed of the diesel engine. In the case where it is possible to measure the pressure in the cylinder accurately during execution of the sub-injection of fuel into the diesel engine, the work, as derived by the pressure in the cylinder, or the pressure in the cylinder itself may be used as the physical quantity.

The output torque of the diesel engine may be found accurately even when the quantity of fuel to be sprayed in the sub-injection is small. The cetane value may, thus, be determined using the output torque when a small quantity of fuel has been sprayed into the diesel engine.

According to another aspect of the invention, there is provided a method of determining a cetane value of fuel to be injected into a diesel engine by a fuel injection system which works to perform, in a cycle, a sub-injection which injects an injection quantity that is a quantity of the fuel smaller than that in a main injection into the diesel engine at a time when the fuel is to be burned in the diesel engine preceding or following the main injection. The method comprises steps of: (a) controlling the fuel injection system to perform a sequence of the sub-injections, a first one of the sub-injections being to spray a first quantity of the fuel as the injection quantity, a following one of the sub-injections being to spray a second quantity of the fuel, as the injection quantity, which is different from the first quantity; (b) acquiring a given physical quantity indicating a state of burning of the diesel engine; (c) determining a physical quantity variation sensitivity which is defined by a ratio of a quantity variation that is a difference between a first value of the physical quantity, as acquired upon execution of the first one of the sub-injections, and a second value of the physical quantity, as acquired upon execution of the following one of the sub-injections, to a difference between the first quantity and the second quantity; and (d) determining a cetane value of the fuel based on a relation between the physical quantity variation sensitivity and the cetane value.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 3 is a flowchart of a sub-program to be executed in the program of FIGS. 2(a) and 2(b) to determine a correction factor to correct the cetane value of the fuel;

FIG. 4 is a flowchart of a sub-program to be executed in the program of FIG. 3 to determine an in-cylinder oxygen-based correction factor to correct the cetane of the fuel;

DESCRIPTION OF THE PREFERRED EMBODIMENTS

Figure 1:
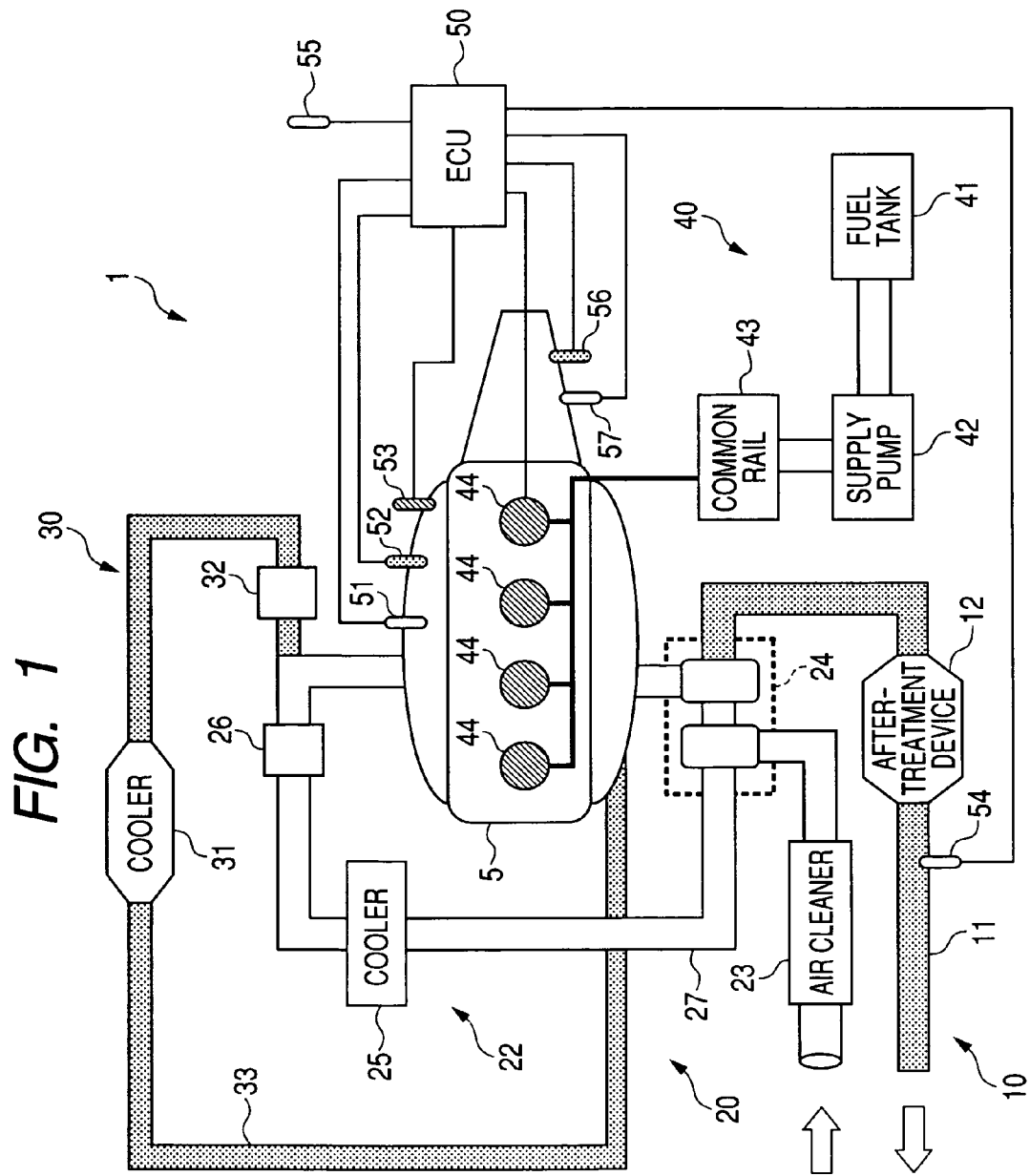
FIG. 1 is a schematic diagram which shows an internal combustion engine control system equipped with a fuel distillation determining apparatus of the present invention.

Referring to the drawings, particularly to FIG. 1, there is shown an internal combustion engine control system 1 according to the invention which is engineered to control an operation of an automotive four-cylinder diesel engine 5. The engine control system 1 includes an exhaust system 10, an air intake system 20, a fuel supply system 40, and an engine ECU (Electronic Control Unit) 50. The exhaust system 20 works to discharge exhaust gas, as emitted from the diesel engine 5, outside the vehicle through an exhaust pipe 11. The air intake system 20 works to mix fresh air with the exhaust gas and supply it to the diesel engine 20. The fuel supply system 40 works to feed fuel such as light oil, as stored in a fuel tank 41, to the diesel engine 50. The ECU 50 works to control the operations of the air intake system 20 and the fuel supply system 40 and also to determine the cetane value (also called cetane number) of the fuel.

The exhaust system 10 is equipped with an after-treatment device 12 which works to deoxidize or reduce nitrogen oxides (NOx) or sulfur oxides (SOx) contained in the exhaust gas emitted from the diesel engine 5. The after-treatment device 12 is installed in the exhaust pipe 11.

The air intake system 20 is equipped with a fresh air supply system 22 and an exhaust gas recirculation system 30. The fresh air supply system 22 works to supply the fresh air to the diesel engine 5. The exhaust gas recirculation system 30 works to recirculate the exhaust gas to the diesel engine 5. The air intake system 20 works to regulate the quantity of the fresh air to be supplied to the diesel engine 5 and the quantity of the exhaust gas to be recirculated to the diesel engine 5.

The fresh air supply system 22 is equipped with an air cleaner 23, a supercharger 24, an air cooler (i.e., an intercooler) 25, and an air regulator valve 26. The air cleaner 23 works to remove dust from the fresh air and deliver it to an intake pipe 27. The supercharger 24 works to compress the fresh air. The air cooler 25 works to cool the fresh air compressed by the supercharger 24. The air regulator valve 26 works to regulate the quantity of the fresh air, as cooled by the air cooler 25, to be supplied to the diesel engine 5. The air cleaner 23, the supercharger 24, the air cooler 25, and the air regulator valve 26 are connected through the intake pipe 27.

The exhaust gas recirculation system 30 is equipped with a recirculating gas cooler 31 and a recirculating gas regulator valve 32. The recirculating gas cooler 31 works to cool the exhaust gas emitted from the diesel engine 5. The recirculating gas regulator valve 32 works to regulate the quantity of the exhaust gas, as cooled by the recirculating gas cooler 31, to be delivered to the diesel engine 5. The recirculating gas cooler 31 and the recirculating gas regulator valve 32 are connected through an EGR pipe 33.

The intake pipe 27 of the fresh air supply system 22 and the EGR pipe 33 of the exhaust gas recirculating system 30 are joined together downstream of the regulator valves 26 and 32, in other words, at a location closer to the diesel engine 5. Specifically, the air intake system 20 is designed to have a recirculation mechanism to recirculate the exhaust gas to deliver a mixture of the exhaust gas and the fresh air to the diesel engine 5. Such a mixture will also be referred to intake air below.

The fuel supply system 40 is equipped with the fuel tank 41, a supply pump 42, a common rail 43, and fuel injectors 44. The supply pump 42 works to pump the fuel out of the fuel tank 41 and pressurize and deliver it to the common rail 43. The common rail 43 stores therein the fuel at a controlled pressure, e.g., 180 Mpa and delivers the fuel to each of the fuel injectors 44. The fuel injectors 44 are installed one in each cylinder of the diesel engine 5 and work to spray the fuel into the cylinders of the diesel engine 5, respectively.

Each of the fuel injectors 44 is equipped with a solenoid-operated valve which is opened in response to a drive pulse signal inputted from the engine ECU 50. The time when the drive pulse signal rises defines the injection timing at which the fuel injectors start to spray the fuel. The width of the drive pulse signal defines the injection duration, that is, the quantity of fuel to be sprayed from the fuel injectors 44.

The internal combustion engine control system 1 also includes an intake air temperature sensor 51, an intake air pressure sensor 52, an intake air composition sensor 53, an A/F (air-fuel ratio) sensor 54, an atmospheric pressure sensor 55, a crank angle sensor 56, and a torque sensor 57. The intake air temperature sensor 51 works to measure the temperature of the intake air charged into the diesel engine 5. The intake air pressure sensor 52 works to measure the pressure of the intake air. The intake air composition sensor 53 works to measure the quantity of oxygen contained in the intake air. The A/F (air-fuel ratio) sensor 54 works to determine the air-fuel ratio of a mixture charged into the diesel engine 5. The atmospheric pressure sensor 55 works to measure the atmospheric pressure. The crank angle sensor 56 works to measure the angular position of a crankshaft of the diesel engine 5. The torque sensor 57 works to measure the torque, as produced by the combustion of fuel in the diesel engine 5. The internal combustion engine control system 1, although not illustrated, also includes an accelerator position sensor to measure the position of an accelerator pedal of the vehicle, a coolant temperature sensor to measure the temperature of coolant of the diesel engine 5, and a rail pressure sensor to measure the pressure of the fuel in the common rail 43.

The engine ECU 50 is implemented by a typical microcomputer made up of a ROM retaining therein logical programs and data even after the engine ECU 50 is turned off, a RAM storing data, as produced temporarily during execution of the programs, and a CPU executing the program, as stored in the ROM or RAM. The engine ECU 50 is connected to all the sensors, as described above, the air regulator valve 26, the recirculating gas regulator valve 32, and the fuel injectors 44 and analyzes inputs from the sensors and control signals to be outputted to determine, at a regular interval (e.g., 0.1 sec.), the speed of the diesel engine 5, an EGR rate (i.e., the quantity of exhaust gas recirculated to the diesel engine 5 (i.e., EGR gas)/(the quantity of fresh air plus the quantity of the EGR gas), the quantity of the intake air sucked into each cylinder of the diesel engine 5, and the oxygen density of the intake air (which is equal to the mass of oxygen in the intake air sucked into the combustion chamber of the diesel engine 5/the volume of a clearance formed above the head of the piston within the combustion chamber of the diesel engine 5 when the piston is at the top-dead center in the compression stroke and which will also be referred to as an in-cylinder oxygen density below).

The ROM of the ECU 50 stores therein a main program, as will be described later in detail, to be executed by the CPU to produce and output the drive pulse signal to each of the fuel injectors 44. The main program is to actuate each of the fuel injectors 44 to perform multiple injections of fuel into the diesel engine 10 in each engine operating cycle (i.e., a four-stroke combustion cycle) including intake or induction, compression, expansion, and exhaust in order to improve the fuel economy and quality of exhaust emissions, and minimize mechanical noise or vibration of the engine. Specifically, the main program is to execute a) a pilot injection to spray a small amount of the fuel to enhance or promote mixing of the fuel and the intake air before it is ignited, b) a pre-injection to reduce the combustion noise, vibration, and NOx emissions contained in the exhaust gas, c) a main injection to move the piston to produce the engine torque, d) an after-injection to re-burn particulate matter (PM), as produced by the combustion of the mixture, and e) a post injection to accelerate the reduction reaction in the after-treatment device 12.

The main injection is the greatest in sprayed quantity of the fuel among the pilot injection, the pre-injection, the after-injection, and the post injection. The fuel sprayed into the diesel engine 5 in the main injection mode is mixed with the intake air, elevated in temperature up to approximately 900K or more in the compression stroke, and then burned to develop the expansion stroke of the piston. The pre-injection of fuel and the after-injection of fuel are usually initiated at the time when the piston lies within a range of the top dead center ±20 deg. to produce a small combustion of the fuel in the cylinder of the diesel engine 5 using the compressed intake air. The pre-injection and the after-injection will also be each referred to as sub-injection below.

Specifically, upon execution of the main program, the ECU 50 samples the outputs from the sensors to determine the injection timing that is the time when each of the above multiple injections should be initiated, select a target quantity of fuel to be sprayed in each of the multiple injections from the RAM until each of the injection timings is reached, and output the drive pulse signal to a corresponding one of the fuel injectors 44 to initiate the spraying of the target quantity of fuel at the determined injection timing. The ECU 50 repeats such a sequence of operations to have the diesel engine 5 continue to run.

Specifically, the internal combustion engine control system 1 executes the main program through the ECU 50 to perform a sequence of five injections: the pilot, pre-, main, after-, and post injections of fuel into the diesel engine 5 through each of the fuel injectors 44 in each of the four-stroke combustion cycles.

Typical internal combustion engine control systems are designed to store therein a predetermined target torque to be produced by the engine as a function of the speed of the engine and also stores data on the temperature of the intake air and a target controlled variable such as a target value of the EGR rate which are required to produce the target torque of the engine and predetermined as a function of the speed of the engine and the target torque of the engine.

Figure 5A:
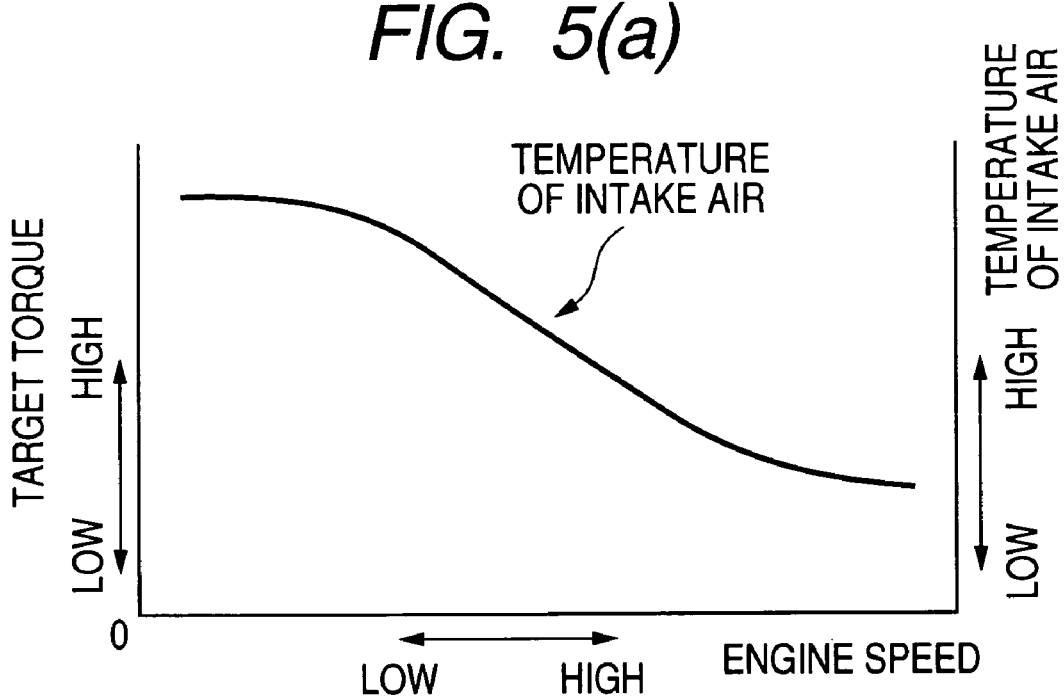
FIG. 5(a) is an illustration which shows an intake air temperature map represents a target value of temperature of intake air as a function of a target torque to be produced by a diesel engine and the speed of the diesel engine.
Figure 5B:
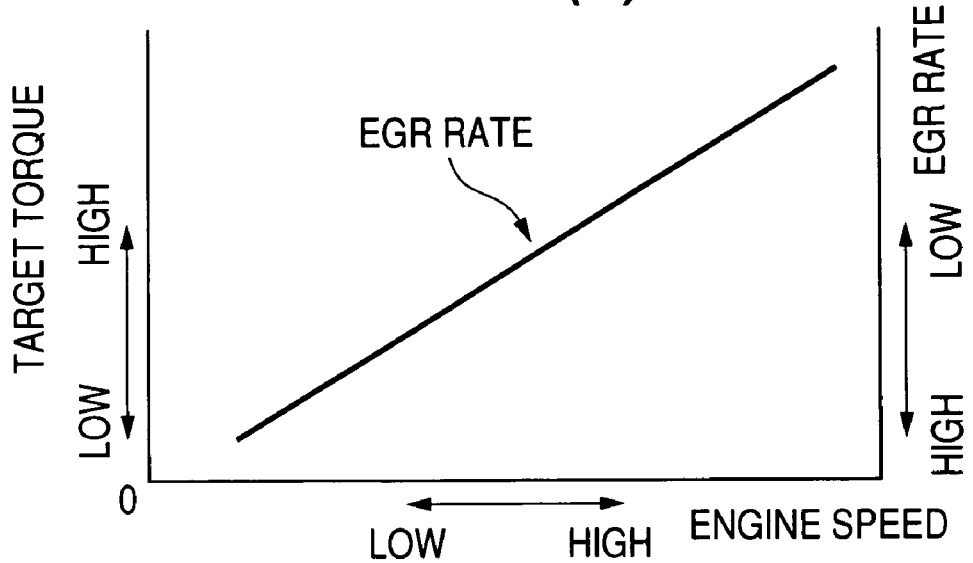
FIG. 5(b) is an illustration which shows an EGR rate map which represents a target value of an EGR rate as a function of a target torque to be produced by a diesel engine and the speed of the diesel engine.

Specifically, the ROM retains therein an intake air temperature map, as demonstrated in FIG. 5(a), and an EGR rate map, as demonstrated in FIG. 5(b). The intake air temperature map represents a target value of the temperature of the intake air as a function of the target torque to be produced by the diesel engine 5 and the speed of the diesel engine 5. The target value of the temperature of the intake air is determined to decrease as the speed of the engine (or the target torque of the engine 5) increases. The EGR rate map represents a target value of the EGR rate as a function of the target torque to be produced by the diesel engine 5 and the speed of the diesel engine 5. The target value of the EGR rate is determined to increase as the speed of the engine (or the target torque of the engine 5) increases.

The ROM also stores therein a computer-executable cetane value determining program, as will be discussed later in detail, which instructs each of the fuel injectors 44 to perform the sub-injections (i.e., the pre-injections in this embodiment) cyclically to spray quantities of fuel different from each other, calculate a torque sensitivity, as defined by a change in torque produced by the diesel engine 5 resulting from a difference between the sprayed quantities of fuel, to determine the cetane value of the fuel, and correct the cetane value as a function of the temperature of the intake air or the in-cylinder oxygen density.

Figure 6:
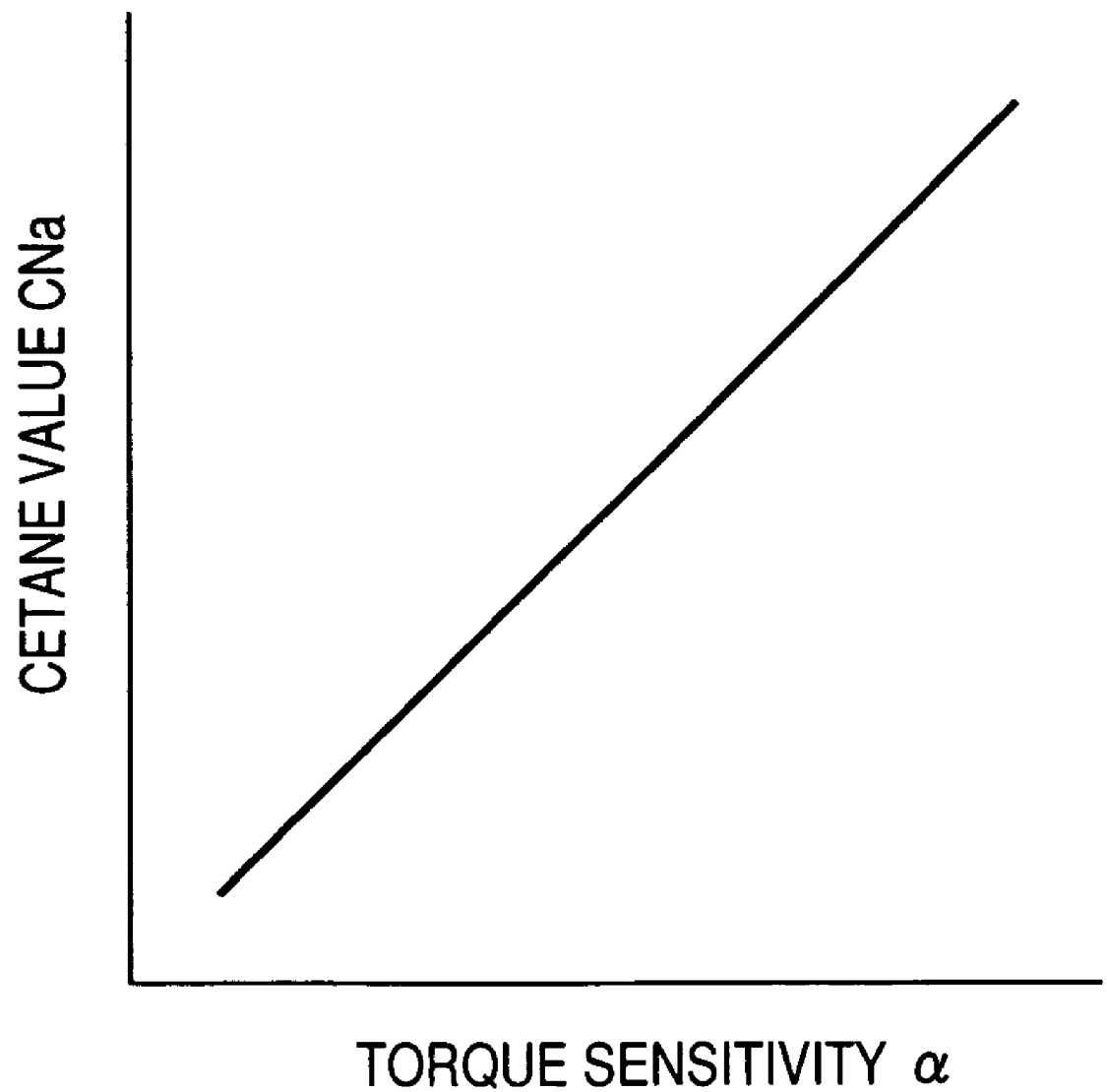
FIG. 6 is an illustration which shows a cetane map which represents an experimentally derived relation of a cetane value to a torque sensitivity.

The ROM also stores therein a cetane map, as illustrated in FIG. 6, which is looked up during execution of the cetane value determining program. The cetane map represents an experimentally derived relation of the cetane value to the torque sensitivity $\alpha$ in which the cetane value increases as an increase with the torque sensitivity $\alpha$. The ROM further stores therein a reference torque map representing a relation of a reference torque g that is a minimum torque to be produced by the diesel engine 5 as a function of the quantity of fuel to be sprayed into the diesel engine 5 in the sub-injection. The reference torque map defines the reference torque g which increases with an increase in the quantity of the fuel to be sprayed.

Figure 7A:
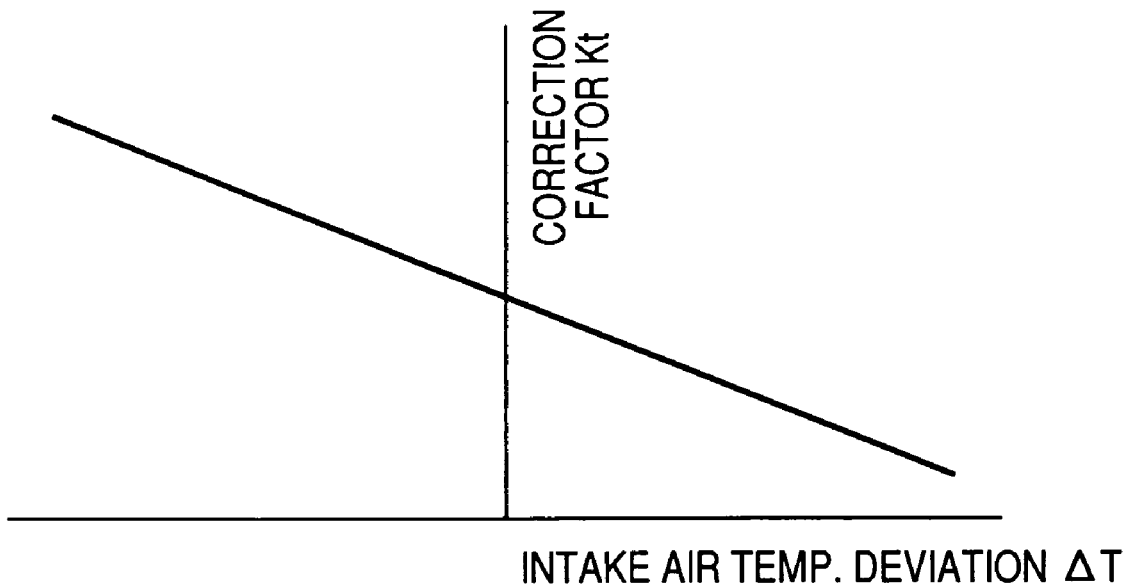
FIG. 7(a) is an illustration which shows an intake air temperature-based correction map which represents an experimentally derived relation of a correction factor Kt to a difference between the temperature of intake air, as derived using the intake air temperature map of FIG. 5(a), and an actual temperature of the intake air.
Figure 7B:
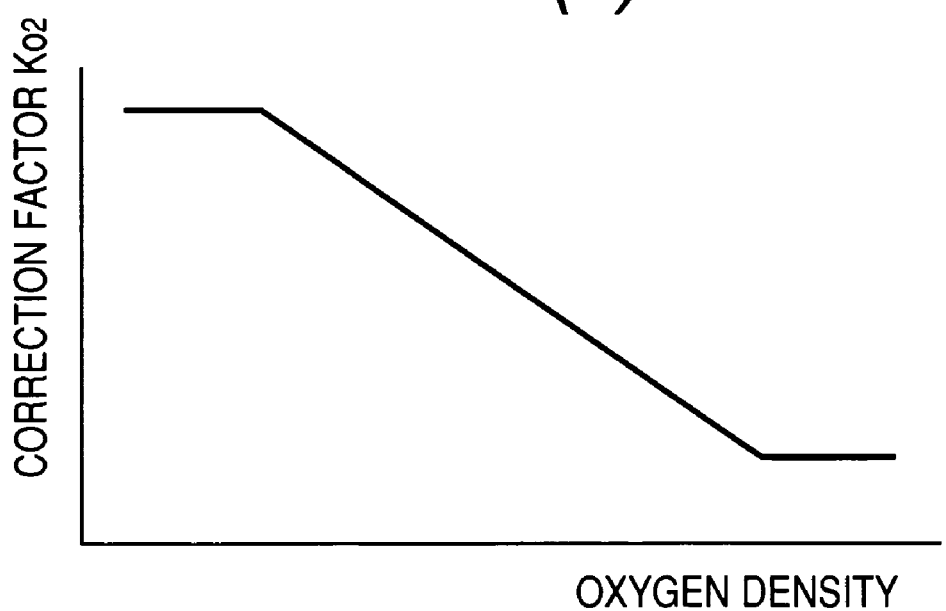
FIG. 7(b) is an illustration which shows an in-cylinder oxygen density-based correction map which represents an experimentally derived relation of a correction factor $Ko_2$ to an in-cylinder oxygen density.
Figure 8:
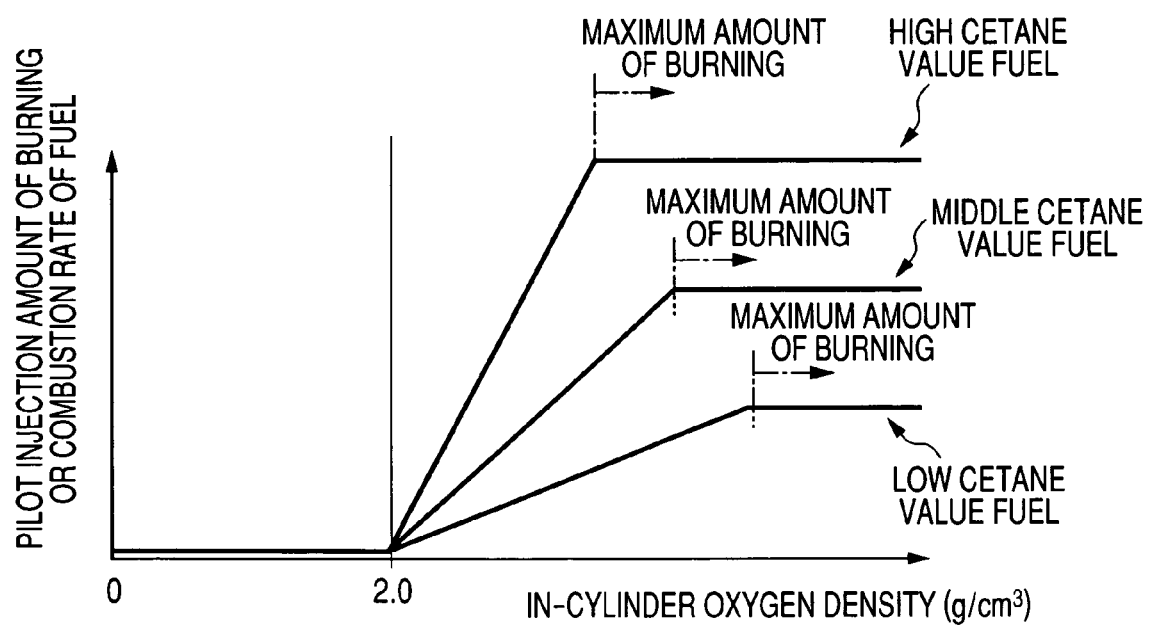
FIG. 8 is an illustration which represents a relation between an oxygen density and burning of a small quantity of fuel in a sub-injection mode.

The ROM also stores therein an intake air temperature-based correction map, as illustrated in FIG. 7(a), and an in-cylinder oxygen density-based correction map, as illustrated in FIG. 7(b). The intake air temperature-based correction map represents an experimentally derived relation of a correction factor Kt (also called a correction value) to a difference between the temperature of the intake air, as derived using the intake air temperature map of FIG. 5(a), which will also be referred to as a reference temperature of the intake air below, and the actual temperature of the intake air. When such a temperature difference is zero (0), the correction factor Kt is determined to be one (1). As the actual temperature of the intake air increases away from the reference temperature, the correction factor Kt is determined to have a smaller value. The in-cylinder oxygen density-based correction map represents an experimentally derived relation of a correction factor $K_{O_2}$ to the in-cylinder oxygen density. When the in-cylinder oxygen density is in a range of zero (0) to a given value (e.g., 2.0 g/cm$^3$), the correction factor $K_{O_2}$ is determined to be one (1). As the in-cylinder oxygen density increases, the correction factor $K_{O_2}$ is determined to have a smaller value.

The engine ECU 50 is designed to perform the main program and the cetane value determining program simultaneously.

Figure 2A:
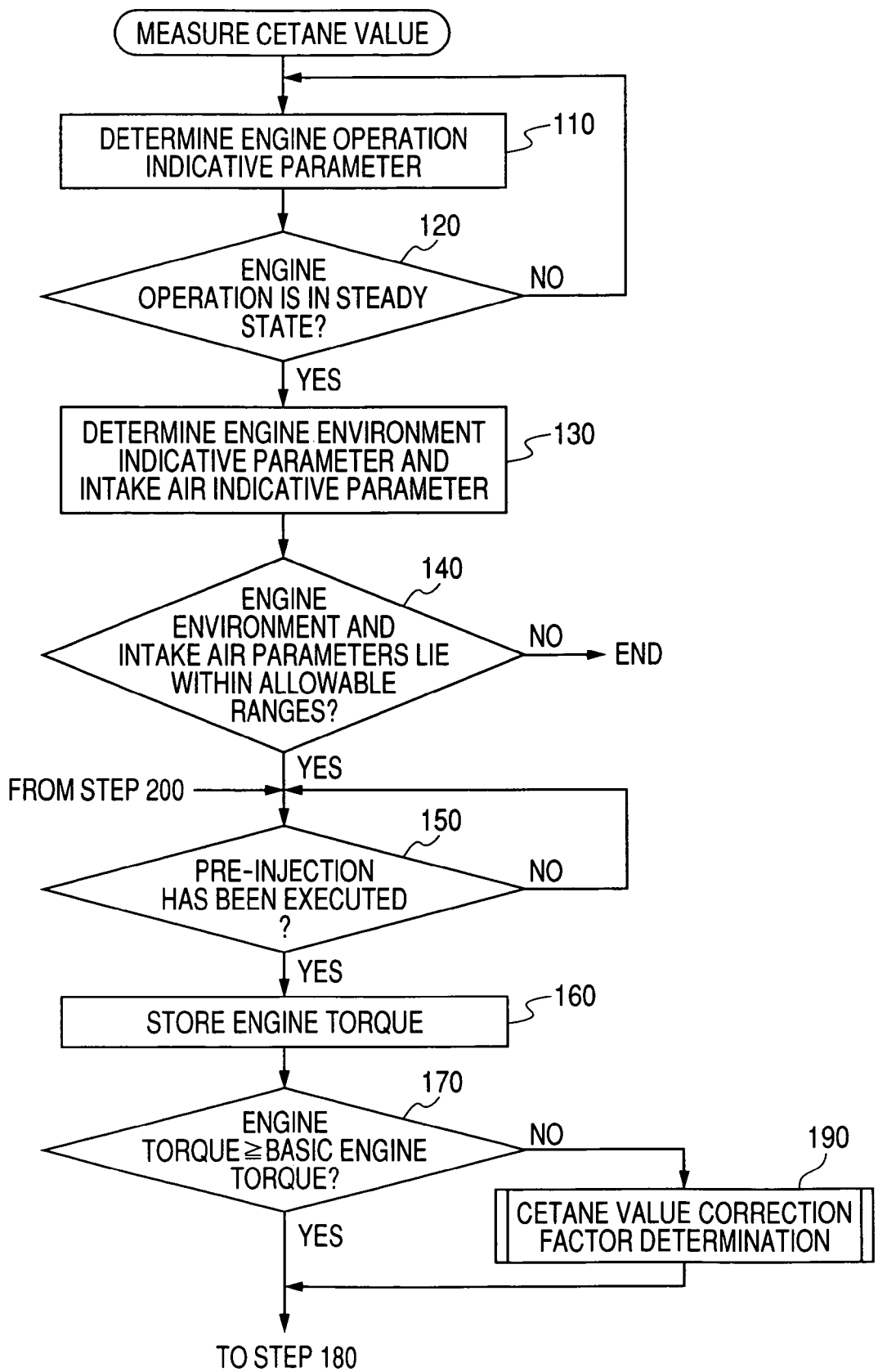
FIGS. 2(a) and 2(b) show a flowchart of a cetane value determining program to be executed by the internal combustion engine control system of FIG. 1 to determine a cetane value of fuel used in a diesel engine.
Figure 2B:
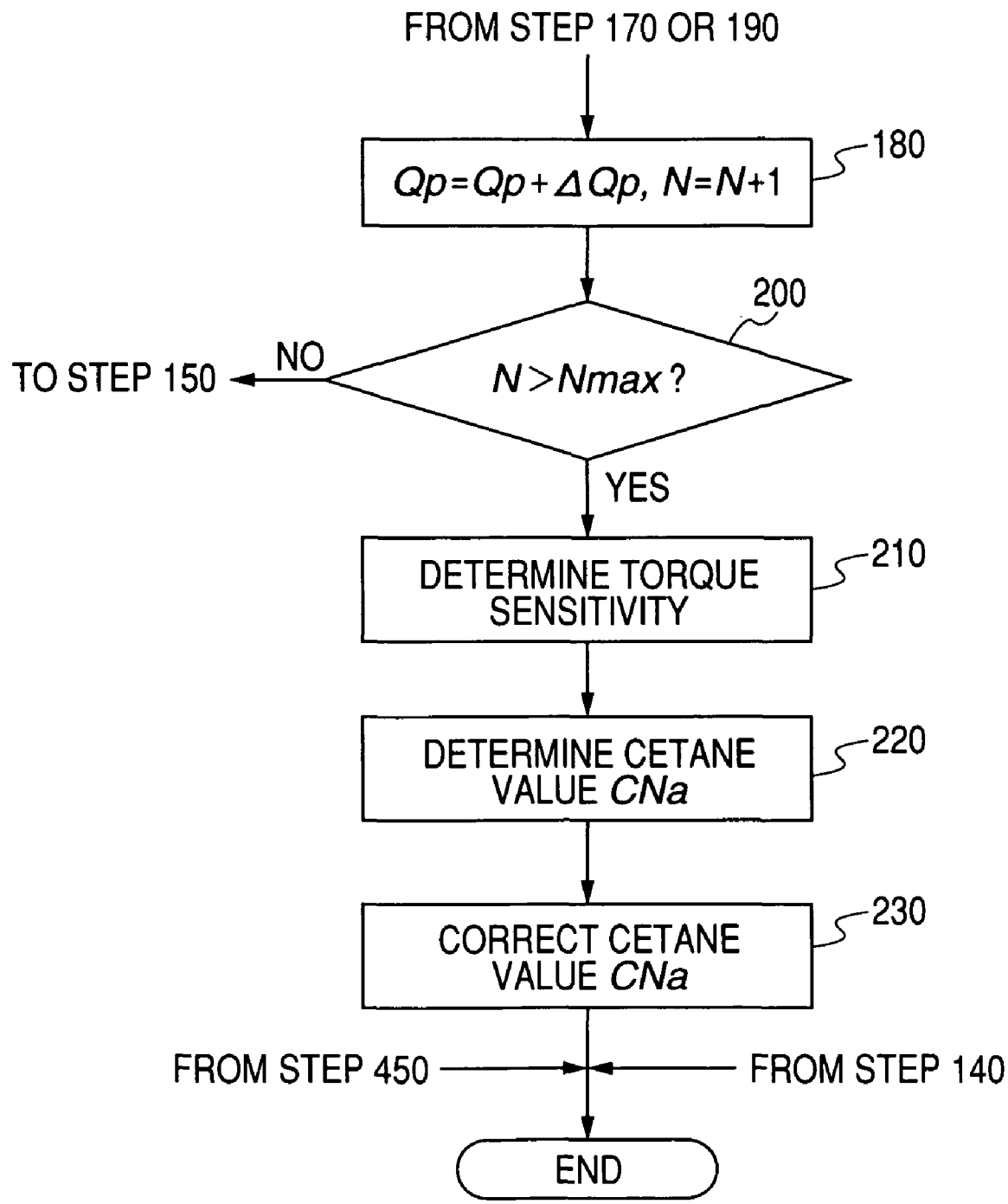

FIGS. 2(a) and 2(b) illustrates a sequence of logical steps of the cetane value determining program which is initiated upon start-up (i.e., turning on of an ignition switch) of the diesel engine 5 for each of the fuel injectors 44

After entering the program, the routine proceeds to step 110 wherein the speed of the diesel engine 5 is monitored at given time intervals to determine an engine speed variation that is a difference in speed of the diesel engine 5 between the time intervals. The engine speed variation is defined as an engine operation indicative parameter. The speed of the diesel engine 5 may be measured by sampling a sequence of outputs from the crank angle sensor 56.

The routine proceeds to step 120 wherein it is determined whether the engine speed variations, as measured cyclically in step 110, continue to lie in a given range for a preselected time (e.g., 1 sec.) or not. In other words, it is determined whether the operation of the diesel engine 5 is now in a steady state or not.

If a NO answer is obtained in step 120 meaning that the engine speed variation is outside the given range, then the routine returns back to step 110. Alternatively, if a YES answer is obtained, then the routine proceeds to step 130 wherein the temperature of the intake air, as measured by the intake air temperature sensor 51, is defined as an engine environment indicative parameter, and the EGR rate calculated in the manner, as discussed above, is defined as an intake air indicative parameter.

The routine proceeds to step 140 wherein it is determined whether the reference temperature of the intake air and the EGR rate which corresponds to the speed of the diesel engine 5, as derived when the operation of the diesel engine 5 is determined to be in the steady state in step 120, are determined by look-up using the intake air temperature map, as illustrated in FIG. 5(*a*), and the EGR rate map, as illustrated in FIG. 5(*b*). Next, it is determined whether the engine environment indicative parameter and the intake air indicative parameter, as derived in step 130, lie within given ranges or not, respectively, which are predefined across the reference temperature of intake air and the EGR rate. For instance, the given ranges are defined to be the reference temperature of intake air ±5% and the EGR rate ±5%, respectively.

If a NO answer is obtained in step 140 meaning that the engine environment indicative parameter and the intake air indicative parameter both do not lie within given ranges, then the routine terminates. Alternatively, if a YES answer is obtained meaning that the cetane value is permitted to be calculated, then the routine proceeds to step 150.

In step 150, a target quantity Qp of fuel to be sprayed in the pre-injection mode is read out of the RAM of the engine ECU 50. The routine waits until the fuel is sprayed in the pre-injection mode from a corresponding one of the fuel injectors 44. Upon execution of the pre-injection, a resulting torque produced by the diesel engine 5 is sampled using the torque sensor 57. When the routine enters step 150 for the first time, a predetermined initial quantity Qpf is selected from the RAM as the target quantity Qp of the fuel to be sprayed into the diesel engine 5.

The routine proceeds to step 160 wherein the engine torque, as sampled in step 150 through the torque sensor 57, is stored in the engine ECU 50 in relation to the target quantity Qp of the fuel sprayed in the pre-injection mode.

The routine proceeds to step 170 wherein the reference torque g which corresponds to the initial quantity Qpf of fuel to be sprayed in the pre-injection mode is read out of the reference torque map stored in the ROM. It is also determined whether the engine torque, as stored in step 160, is greater than or equal to the reference torque g or not. If a YES answer is obtained meaning that the engine torque is greater than or equal to the reference torque g, the routine then proceeds to step 180.

Alternatively, if a NO answer is obtained in step 170, then the routine proceeds to step 190 wherein a cetane value correction factor determining program is executed. Specifically, it is determined whether the factor contributing to the fact that the engine torque, as created in the pre-injection in step 150, is less than the reference torque g is caused by the temperature of the intake air or the in-cylinder oxygen density. The correction factor Kt or the correction factor $Ko_2$ is selected according to that fact from the intake air-based correction map, as illustrated in FIG. 7(*a*), the in-cylinder oxygen density-based correction map, as illustrated in FIG. 7(*b*), for correcting the cetane value of the fuel.

The cetane value correction factor determining program will be described below with reference to a flowchart of FIG. 3.

First, in step 310, a second increment ΔQp2 is added to the quantity Qp of fuel sprayed in the pre-injection mode in step 150. The sum of the second increment ΔQp2 and the quantity Qp is defined as the injection quantity Qp and stored in the RAM.

Next, in step 320, the routine waits until the injection quantity Qp of fuel, as derived in step 310, is sprayed in the pre-injection mode from a corresponding one of the fuel injectors 44. Upon execution of the pre-injection mode, a resulting torque produced by the diesel engine 5 is sampled using the torque sensor 57.

The routine then proceeds to step 330 wherein the engine torque, as sampled in step 320 through the torque sensor 57, is stored in the engine ECU 50 in relation to the sum of the second increments ΔQp2 which have been added totally to the injection quantity Qp (which will be referred to as a total pre-injection quantity increment ΣΔQp2).

The routine proceeds to step 340 wherein the temperature of the intake air (will also be referred to as a reference intake air temperature below) corresponding to the injection quantity Qp, as sprayed in the pre-injection mode in step 320, is selected from the intake air temperature map in the ROM, and a difference between the reference intake air temperature and an actual temperature of the intake air, as determined upon entry in step 340, (which will also be referred to as an intake air temperature deviation ΔT below) is calculated. Note that the injection quantity Qp has a predetermined relation to the speed of the diesel engine 5.

The routine proceeds to step 350 wherein it is determined whether the engine torque, as stored in step 330, is greater than or equal to the reference torque g, as derived in step 170, or not. If a YES answer is obtained meaning that the engine torque is greater than or equal to the reference torque g, and the factor causing a lack of the engine torque outputted by the diesel engine 5 is associated with the temperature of the intake air, then the routine proceeds to step 380.

In step 380, the intake air temperature-based correction factor Kt corresponding to the intake air temperature deviation ΔT, as derived in step 340, is selected from the intake air temperature-based correction map, as illustrated in FIG. 7(*a*). The routine then returns back to step 180.

If a NO answer is obtained is step 350 meaning that the engine torque is less than the reference torque g, then the routine proceeds to step 360 wherein it is determined whether the total pre-injection quantity increment ΣΔQp2, as stored in step 330, is greater than or equal to a given upper increment limit $Qp2_{MAX}$ or not. If a NO answer is obtained meaning that the total pre-injection quantity increment ΣΔQp2 is less than the upper increment limit $Qp2_{MAX}$, then the routine returns back to step 310 and repeats a sequence of steps 310 to 350.

Alternatively, if a YES answer is obtained in step 360 meaning that the factor causing the lack of the engine torque outputted by the diesel engine 5 is associated with other than the temperature of the intake air, then the routine proceeds to step 370 wherein an oxygen density-based correction factor determination is made to select the in-cylinder oxygen-based correction factor $Ko_2$ from the in-cylinder oxygen-based correction map, as illustrated in FIG. 7(*b*), for correcting the cetane value.

Specifically, in the cetane value correction factor determining program, when the factor causing the lack of the engine torque is determined to be associated with the temperature of the intake air, the engine ECU 50 selects the intake air temperature-based correction factor Kt (less than one (1)) which decreases as the intake air temperature deviation ΔT increases. Alternatively, when the factor causing the lack of the engine torque is determined not to be associated with the temperature of the intake air, the engine ECU 50 commences an in-cylinder oxygen density-based correction factor determining program, as will be described in detail below.

FIG. 4 illustrates a sequence of logical steps to determine the in-cylinder oxygen-based correction factor $Ko_2$.

First, in step 410, the engine ECU 50 outputs control signals to the air regulator valve 26 and the recirculating gas regulator valve 32 to increase the quantity of oxygen in the intake air by a given oxygen increment $\Delta O_{2d}$. Specifically, the air regulator valve 26 and the recirculating gas regulator valve 32 are actuated by the control signals to change the open position thereof to increase the quantity of oxygen in the intake air for increasing the in-cylinder oxygen density.

Next, in step 420, the routine waits until the injection quantity Qp of fuel, as stored in the RAM, is sprayed in the pre-injection mode from the fuel injector 44. Upon execution of the pre-injection mode, a resulting torque produced by the diesel engine 5 is sampled using the torque sensor 57. Note that the injection quantity Qp stored in the RAM is a maximum quantity of the fuel which has been increased up to the upper increment limit $Qp2_{MAX}$.

The routine then proceeds to step 430 wherein the engine torque, as sampled in step 420 through the torque sensor 57, is stored in the engine ECU 50 in relation to the sum of the oxygen increments $\Delta O_{2d}$ which have been added totally to the quantity of the intake air (which will be referred to as a total oxygen quantity increment $\Sigma \Delta O_{d2}$).

The routine proceeds to step 440 wherein it is determined whether the engine torque, as stored in step 430, is greater than or equal to the reference torque g, as derived in step 170, or not. If a NO answer is obtained meaning that the engine torque is less than the reference torque g, then the routine proceeds to step 450.

In step 450, it is determined whether the total oxygen quantity increment $\Sigma \Delta O_{2d}$, as stored in step 430, is greater than or equal to a given upper increment limit $O_{2d}h$ or not. If a NO answer is obtained meaning that the total oxygen quantity increment $\Sigma \Delta O_{2d}$ is less than the upper increment limit $O_{2d}h$, the routine returns back to step 410 and repeats a sequence of steps 410 and 440.

Alternatively, if a YES answer is obtained in step 450 meaning that the total oxygen quantity increment $\Sigma \Delta O_{2d}$ is greater than or equal to the upper increment limit $O_{2d}h$, the routine then terminates.

If a YES answer is obtained in step 440 meaning that the engine torque is greater than or equal to the reference torque g, and the factor causing the lack of the engine torque outputted by the diesel engine 5 is associated with the in-cylinder oxygen density, then the routine proceeds to step 460.

In step 460, the value of the in-cylinder oxygen-based correction factor $K_{O2}$ corresponding to the total oxygen quantity increment $\Sigma \Delta O_{2d}$, as stored in step 430, is selected from the in-cylinder oxygen density-based correction map, as illustrated in FIG. 7(b). The routine then returns back to step 180.

Specifically, when the factor causing the lack of the engine torque is determined to be associated with the in-cylinder oxygen density, and the total oxygen quantity increment $\Sigma \Delta O_{2d}$ is greater than or equal to a given reference value, the engine ECU 50 selects the value of the in-cylinder oxygen-based correction factor $K_{O2}$ (less than one (1)) which decreases as the total oxygen quantity increment $\Sigma \Delta O_{2d}$ increases. Alternatively, when the factor causing the lack of the engine torque is determined not to be associated with the temperature of the intake air or the in-cylinder oxygen density, the engine ECU 50 terminates the cetane value determining program without determining the cetane value of the fuel.

After step 370 or 380 the routine returns back to step 180 of FIG. 2. In step 180, the injection quantity Qp now stored in the RAM is read out, increased by a given first increment $\Delta Qp$ and stored in the RAM as the injection quantity Qp. Additionally, a count value N is incremented by one (1).

Specifically, when the routine proceeds to step 180 after the cetane value correction factor determining program of FIG. 3 is completed in this execution cycle of the cetane value determining program of FIGS. 2(a) and 2(b), the injection quantity Qp which has been increased in the cetane value correction factor determining program (i.e., the sum of initial quantity Qpf and the total pre-injection quantity increment $\Sigma \Delta Qp2$) is further incremented by a given first increment $\Delta Qp$. Alternatively, when the routine proceeds to step 180 without performing step 190 in this execution cycle of the cetane value determining program, in other words, if a YES answer is obtained in step 170, the injection quantity Qp that is the quantity of fuel having been sprayed in step 150 is incremented by the first increment $\Delta Qp$.

In the following discussion, the injection quantity Qp which is to be stored in the RAM when the routine first proceeds to step 180 will be referred to as an initial injection quantity Qp1 below.

After step 180, the routine proceeds to step 200 wherein it is determined whether the count value N is greater than or equal to a maximum value Nmax (e.g., 6) or not. If a NO answer is obtained meaning that the count value N is less than maximum value Nmax, then the routine returns back to step 150 and performs a sequence of steps 150 to 180 again. Once the cetane value correction factor determining program is performed, the ECU 50 increases the quantity of fuel sprayed into the diesel engine 5 and the quantity of oxygen in the intake air, so that the torque outputted by the diesel engine 5 is increased over the reference torque g. This results in a decrease in possibility of re-execution of the cetane value correction factor determining program. Specifically, only when the output torque of the diesel engine 5 has exceeded the reference torque g in the cetane value correction factor determining program executed in step 190, the routine returns back to the cetane value determining program (i.e., step 180). The possibility that the cetane value correction factor determining program will be performed in the second execution cycle or later is, therefore, low.

Alternatively, if a YES answer is obtained in step 200 meaning that the count value N is greater than or equal to a maximum value Nmax, then the routine proceeds to step 210 wherein the torque (which will be referred to as an initial engine torque below) produced by the diesel engine 5 when the initial injection quantity Qp1 of the fuel has been sprayed in the pre-injection mode and the torque (which will be referred to as a changed engine torque below) produced by spraying the injection quantity Qp of the fuel (i.e., Qp=Qp1+ 4×$\Delta Qp$) into the diesel engine 5 in the pre-injection mode when the count value N is Nmax minus one (1) are read out of the RAM. A difference between the initial engine torque and the changed engine torque is calculated as an engine torque change. A ratio of the engine torque change to an increment of the injection quantity Qp (i.e., 4×$\Delta Qp$) is calculated as the torque sensitivity α. Specifically, the torque sensitivity is determined by dividing the engine torque change by the increment of the injection quantity Qp.

The routine then proceeds to step 220 wherein the cetane value CNa corresponding to the torque sensitivity α, as derived in step 210, is read out of the cetane map, as illustrated in FIG. 6.

The routine proceeds to step 230 wherein the cetane value CNa, as determined in step 220, is multiplied by the intake air temperature-based correction factor Kt or the in-cylinder oxygen density-based correction factor $K_{O2}$, as derived in the cetane value correction factor determining program, as described above, to produce a cetane value CN. Note that if the intake air temperature-based correction factor Kt or the in-cylinder oxygen density-based correction factor $K_{O2}$ is not yet been found, the cetane value CNa is multiplied by one (1) and defined as the cetane value CN. The cetane value CN is then stored in the RAM after which the cetane value determining program terminates.

The engine ECU 50 works to use the cetane value CN, as determined in the above manner, for correcting the target quantity of fuel to be sprayed and the injection timing in the main or sub-injection modes.

Specifically, when the diesel engine 5 is running in the steady state, and the engine environment indicative parameter and the intake air indicative parameter both lie in the allowable ranges, the engine ECU 50 determines the initial quantity Qp1 as the target injection quantity Qp and sprays the target injection quantity Qp of fuel into the diesel engine 5 in the pre-injection mode. The engine ECU 50 also samples a resulting torque outputted by the diesel engine 5 and determines whether that output torque is greater than the reference torque g or not. When the output torque is smaller than the reference torque g, that is, when the diesel engine 5 has failed to produce the required torque, the engine ECU 50 commences the cetane value correction factor determining program of FIG. 3. When the factor causing the lack of the output torque is found to be associated with the temperature of the intake air, the engine ECU 50 derives the intake air temperature-based correction factor Kt. Alternatively, when the factor causing the lack of the output torque is found to be associated with the in-cylinder oxygen density, the engine ECU 50 derives the in-cylinder oxygen density-based correction factor $K_{O2}$.

When there is no lack of the output torque or the factor causing the lack of the output torque has been eliminated, the engine ECU 50 sprays the initial injection quantity Qp1 of fuel and the injection quantity that is greater than the initial injection quantity Qp1 by the first increment ΔQp in the pre-injection mode, samples resulting torques outputted from the diesel engine 5, and calculates the torque sensitivity based on the sampled output torques and the increment of the injection quantity Qp. The engine ECU 50 determines the cetane value CNa based on the torque sensitivity. When either the intake air temperature-based correction factor Kt or the in-cylinder oxygen density-based correction factor $K_{O2}$ is derived, the engine ECU 50 multiplies the cetane value CNa by the derived one of them to determine the cetane value CN.

As apparent from the above discussion, the ECU 50 is designed to determine the cetane value of the fuel used to operate the diesel engine 5 using the torque sensitivity which hardly changes with a change in operating condition or operating environment of the diesel engine 5, thus resulting in increased accuracy in determining the cetane value of the fuel.

When the output torque of the diesel engine 5 produced by the pre-injection of the initial quantity Qpf of fuel thereinto is less than the reference torque g, the engine ECU 50 determines the correction factor to correct the cetane value based on the factor causing the output torque to be lower than the reference torque g, thus resulting in improved accuracy in determining the cetane value of the fuel.

The factor causing the lack of the engine torque outputted by the diesel engine 5 is achieved in the cetane value correction factor determining program by incrementing the quantity of fuel to be sprayed into the diesel engine 5 or the quantity of oxygen in the intake air, thus permitting the cetane value of the fuel to be corrected with minimum adverse effects on the operation of the diesel engine 5. In the in-cylinder oxygen density-based correction factor determining program of FIG. 4, as long as the output torque of the diesel engine 5 is lower than the reference torque g, the engine ECU 50 increases the quantity of oxygen in the intake air. This keeps the in-cylinder oxygen density at a level required to ensure the burning of the fuel in the diesel engine 5.

The engine ECU 50 analyzes the cetane value of the fuel, as determined in the above manner, to control the timing of the pilot, the pre-, the main, the after-, and the post injection of the fuel into the diesel engine 5, the quantity of the fuel to be injected, and the quantity of the exhaust gas to be recirculated to the cylinders of the diesel engine 5 for reducing harmful emissions such as NOx, smoke, HC, and CO from the diesel engine 5.

Specifically, the engine ECU 50 is designed to determine the cetane value of the fuel correctly without use of an additional sensor, thereby permitting the internal combustion engine control system 1 to be manufactured at low costs while ensuring the accuracy of determination of the cetane value.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

For example, when a variation in speed of the diesel engine 5 continues to lie within the given range, that is, when the operation of the diesel engine 5 is in the steady state, the cetane value determining program allows the cetane value to be determined, but however, an additional condition where the speed of the diesel engine 5 indicates the idling mode of engine operation or the diesel engine 5 is decelerating, that is, the diesel engine 5 is undergoing a fuel cut may be used in allowing the cetane value to be determined in order to increase the accuracy in determining the cetane value.

The engine ECU 50, as described above, determines whether the operation of the diesel engine 5 is in the steady state or not based on the speed thereof, however, such a determination may be made based on the quantity of fuel to be sprayed into the diesel engine 5 in the main injection mode. For instance, when a variation in quantity of fuel to be sprayed in the main injection mode continues to lie within a given range, the engine ECU 50 may determine that the operation of the diesel engine 5 is in the steady state.

The engine environment indicative parameter is, as described above, defined by the temperature of the intake air, however, may additionally be defined by the atmospheric pressure. For example, when the temperature of the intake air is within an allowable range, and the atmospheric pressure is higher than a given set level, the engine ECU 50 preferably permits the cetane value to be determined. In other words, the engine ECU 50 may prohibit the determination of the cetane value when the automotive vehicle in which the diesel engine 5 is mounted is running at altitudes of more than a predetermined level.

The intake air indicative parameter is defined only by the EGR rate, however, may additionally be defined by the quantity of the intake air or the temperature of the intake air. For example, when at least one of the EGR rate, the quantity of the intake air, and the temperature of the intake air is within a given allowable range, the engine ECU 50 may permit the cetane value to be determined.

The cetane value determining program permits the cetane value to be determined when both the engine environment indicative parameter and the intake air indicative parameter lie within the given ranges, however, such a determination may alternatively be permitted when either of the engine environment indicative parameter and the intake air indicative parameter lies within the given range. Additionally, the cetane value may be permitted to be determined regardless of the engine environment indicative parameter and the intake air indicative parameter. Specifically, the determination of the cetane value may be permitted only based on the engine operation indicative parameter.

The cetane value may be permitted to be determined when an additional condition where the automotive vehicle in which the diesel engine 5 is mounted has been refueled is met. Such a condition may be found by monitoring whether a filler cap has been opened or not or the amount of fuel in a fuel tank has been increased or not.

The engine ECU 50 is designed to measure the output torque of the diesel engine 5 using the torque sensor 57, but such a measurement may be made based on a variation in crank angle, as sampled by the crank angle sensor 56 or in another known manner.

The torque sensitivity is, as described above, determined by dividing the engine torque change by the increment of the injection quantity Qp, however, it may be derived by measuring an increment of the output torque of the diesel engine 5 each increment of the injection quantity Qp, calculating an average of divisions of the increments of the output torque by the increments of the injection quantity Qp, and defining it as the torque sensitivity.

The cetane value determining program uses the output torque of the diesel engine 5 as a physical quantity to derive a parameter (i.e., the torque sensitivity) for determining the cetane value of the fuel, however, the amount of burned fuel in the sub-injection mode, a variation in speed of the diesel engine in the sub-injection mode, or a work derived thereby may be used as the physical quantity. Specifically, a physical quantity which changes linearly with a change in quantity of fuel sprayed in the sub-injection mode may be used as the parameter for determining the cetane value of the fuel.

The intake air temperature-based correction map may be so made as to indicate a relation of the correction factor Kt to an increment of the injection quantity Qp or to the intake air temperature deviation ΔT for each of the incremented injection quantities Qp. The in-cylinder oxygen density-based correction map may also be so made as to indicate a relation of the correction factor $K_{O2}$ to an increment of the quantity of oxygen in the intake air for each temperature of the intake air.

The oxygen density of the intake air is, as described above, calculated by dividing the mass of oxygen in the intake air sucked into the combustion chamber of the diesel engine 5 by the volume of the clearance above the head of the piston within the combustion chamber of the diesel engine 5 when the piston is at the top-dead center, however, it may be derived by dividing the mass of oxygen in the intake air by the volume of the cylinder of the diesel engine 5 or the mass of a total amount of the intake air which has been sucked into the engine in each combustion cycle of the diesel engine 5.

The engine ECU 50 may alternatively be designed to calculate the correction factor Kt or $K_{O2}$ mathematically without use of the map, as illustrated in FIG. 7(a) or 7(b).

The cetane value determining program changes the injection quantity Qp by the first increment ΔQp to determine the correction factor for the cetane value, however, it may alternatively be designed to decrease the injection quantity Qp by an amount identical with the first increment ΔQp. In this case, the initial quantity Qpf of fuel to be sprayed into the diesel engine 5 needs to be selected so that a resulting output torque of the diesel engine 5 will be greatly higher than the reference torque g. The first and second increments ΔQp and ΔQp2 may be selected to be constant or changed each time it is required to change the injection quantity Qp.

The cetane value determining program works to control the quantity of fuel to be sprayed into the diesel engine 5 in the pre-injection mode to determine the cetane value of the fuel, however, it may be designed to control the quantity of fuel to be sprayed in the after-injection mode or another injection mode in which a quantity of fuel smaller than that in the main injection mode is to be sprayed into the diesel engine 5. Specifically, the engine ECU 50 may spray a small quantity of fuel into the diesel engine 5 at the time when the fuel is to be burned in the diesel engine 5 before or after execution of the main injection mode.

The internal combustion engine control system 1 may alternatively be designed to be mounted in vehicles such as railway diesel locomotives other than automobiles.

What is claimed is:

1. A fuel distillation property determining apparatus designed to determine a cetane value of fuel to be injected into a diesel engine by a fuel injection system which works to perform, in a cycle, a sub-injection which injects an injection quantity that is a quantity of the fuel smaller than that in a main injection into the diesel engine at a time when the fuel is to be burned in the diesel engine preceding or following the main injection, comprising:

sub-injection control means for controlling the fuel injection system to perform a sequence of the sub-injections, a first one of the sub-injections being to spray a first quantity of the fuel as the injection quantity, a following one of the sub-injections being to spray a second quantity of the fuel as the injection quantity which is different from the first quantity;

physical quantity acquiring means for acquiring a given physical quantity indicating a state of burning of the fuel in the diesel engine;

physical quantity variation sensitivity determining means for determining a physical quantity variation sensitivity which is defined by a ratio of a quantity variation that is a difference between a first value of the physical quantity, as acquired upon execution of the first one of the sub-injections, and a second value of the physical quantity, as acquired upon execution of the following one of the sub-injections, to a difference between the first quantity and the second quantity; and fuel distillation property determining means for determining a cetane value of the fuel based on a predefined relation between the physical quantity variation sensitivity and the cetane value.

2. A fuel distillation property determining apparatus as set forth in claim 1, further comprising engine environment indicative parameter acquiring means for acquiring an engine environment indicative parameter representing an engine operating environment when the diesel engine is running, engine operation indicative parameter acquiring means for acquiring an engine operation indicative parameter representing an operating condition of the diesel engine, intake air indicative parameter acquiring means for acquiring an intake air indicative parameter representing a status of intake air to be sucked into a cylinder of the diesel engine; and cetane value determination permission means for permitting said fuel distillation property determining means to determine the cetane value when at least one of the engine environment indicative parameter, the engine operation indicative parameter, and the intake air indicative parameter is in a given permissible range.

3. A fuel distillation property determining apparatus as set forth in claim 2, further comprising factor determining means for determining whether the first value, as acquired upon execution of the first one of the sub-injections, lies out of a given range or not which is defined based on a value of the physical quantity which is to appear when the sub-injection is executed, wherein when it is determined that the first value is out of the given range, and said cetane value determination permission means permits said fuel distillation property determining means to determine the cetane value, said factor determining means makes a determination of which of a temperature of intake air and an in-cylinder oxygen density is a factor causing the first value to lie out of the given range, the temperature of the intake air being a temperature of air to be sucked into a cylinder of the diesel engine, the in-cylinder oxygen density being a density of oxygen contained in the air sucked in the cylinder of the diesel engine, and further comprising correcting means for correcting the cetane value, as derived by said fuel distillation property determining means, based on the determination of said factor determining means.

4. A fuel distillation property determining apparatus as set forth in claim 3, wherein said factor determining means includes injection quantity changing means and intake air flow controlling means, said injection quantity changing means changing the injection quantity by a given amount each time the sub-injection is made until a total of the amounts reaches an upper limit, after said injection quantity changing means changes the injection quantity until the total of the amounts reaches the upper limit, said intake air flow controlling means controlling a regulator mechanism which works to mix atmospheric air with exhaust gas emitted from the diesel engine to produce the intake air and regulate a quantity of the atmospheric air and a quantity of the exhaust gas in the intake air to increase the in-cylinder oxygen density, when the physical quantity, as acquired by said physical quantity acquiring means, falls in the given range before the injection quantity in the sub-injection, as changed by said injection quantity changing means, reaches the upper limit, said factor determining means determining the temperature of intake air as being the factor causing the first value to lie out of the given range, when the physical quantity, as acquired by said physical quantity acquiring means, falls in the given range upon execution of the sub-injection after the in-cylinder oxygen density is increased by the intake air flow controlling means, said factor determining means determining the in-cylinder oxygen density as being the factor causing the first value to lie out of the given range.

5. A fuel distillation property determining apparatus as set forth in claim 3, wherein said correcting means includes oxygen density determining means for determining the in-cylinder oxygen density, and wherein when said factor determining means determines the in-cylinder oxygen density as being the factor causing the first value to lie out of the given range, said correcting means corrects the cetane value so as to decrease as the in-cylinder oxygen density, as determined by said oxygen density determining means, is higher than a given oxygen density.

6. A fuel distillation property determining apparatus as set forth in claim 3, wherein said correcting means includes temperature determining means for determining the temperature of the intake air, and when said factor determining means determines the temperature of the intake air as being the factor causing the first value to lie out of the given range, said correcting means corrects the cetane value so as to decrease as a value of the temperature of the intake air, as determined by said temperature determining means, becomes higher than a value of the temperature of the intake air when being in the given permissible range.

7. A fuel distillation property determining apparatus as set forth in claim 1, wherein the physical quantity, as acquired by said physical quantity acquiring means, is one of a work of the diesel engine and a variation in speed of the diesel engine.

8. A method of determining a cetane value of fuel to be injected into a diesel engine by a fuel injection system which works to perform, in a cycle, a sub-injection which injects an injection quantity that is a quantity of the fuel smaller than that in a main injection into the diesel engine at a time when the fuel is to be burned in the diesel engine preceding or following the main injection, comprising the steps of:
controlling the fuel injection system to perform a sequence of the sub-injections, a first one of the sub-injections being to spray a first quantity of the fuel as the injection quantity, a following one of the sub-injections being to spray a second quantity of the fuel, as the injection quantity, which is different from the first quantity;
acquiring a given physical quantity indicating a state of burning of the diesel engine;
determining a physical quantity variation sensitivity which is defined by a ratio of a quantity variation that is a difference between a first value of the physical quantity, as acquired upon execution of the first one of the sub-injections, and a second value of the physical quantity, as acquired upon execution of the following one of the sub-injections, to a difference between the first quantity and the second quantity; and
determining a cetane value of the fuel based on a relation between the physical quantity variation sensitivity and the cetane value.

* * * * *